United States Patent [19]

Schiehser et al.

[11] Patent Number: 5,070,207
[45] Date of Patent: Dec. 3, 1991

[54] PHOSPHOLIPASE A2 INHIBITORS

[75] Inventors: Guy A. Schiehser, Yardley, Pa.;
Gregory F. Von Burg, Princeton, N.J.

[73] Assignee: American Home Products Corporation, New York, N.Y.

[21] Appl. No.: 516,023

[22] Filed: Apr. 26, 1990

[51] Int. Cl.$^5$ ............... C07D 275/04; C07D 209/82;
C07D 49/213; C07D 49/115
[52] U.S. Cl. ........................ 548/208; 548/437;
548/444; 568/308; 568/326; 568/328
[58] Field of Search ............... 548/437, 208, 444;
568/308, 326, 328

[56] References Cited

U.S. PATENT DOCUMENTS

| | | | |
|---|---|---|---|
| 4,551,264 | 11/1985 | Eidenschink et al. | 252/299.1 |
| 4,564,694 | 1/1986 | Hirai et al. | 560/1 |
| 4,886,619 | 12/1989 | Janulis | 252/299.62 |

OTHER PUBLICATIONS

Chemical Abstracts vol. 112: 7354h, Kitatsume et al., Abstracts of Jpn Kokai Tokkyo Koho JP01,135,781, May 29, 1989.
Chemical Abstracts vol. 112: 54175w, Kitatsume et al. Abstract of Jpn Kokai Tokkyo Koho JP 01,135,738, May 29, 1989.
Chemical Abstracts vol. 113: 39,510t, Kuroboshi et al. Abstract of Bull. Chem. Soc. Jpn. (1990) 63(2) 428-37.
Copy of Chemical Abstracts Structural Search Output with Cross Reference to R and S above.
Il Farmaco—Ed. Sc., 39(5), 403-13 (1984).
Pesticide Biochemistry and Physiology, 17, 89-95 (1982).
J. Org. Chem., 48, 1925-26 (1983).
J. Fluorine Chem., 30, 189-202 (1985).

Primary Examiner—Mukund J. Shah
Assistant Examiner—Matthew V. Grumbling
Attorney, Agent, or Firm—George Tarnowski

[57] ABSTRACT

There is disclosed a method for the treatment of immunoinflammatory conditions, such as allergy, anaphylaxis, asthma, psoriasis, inflammatory bowel disease and inflammation in mammals which comprises administering to a mammal so afflicted an effective amount of a compound having the formula:

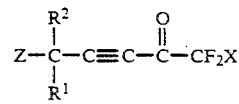

wherein
Z is a group having the formula

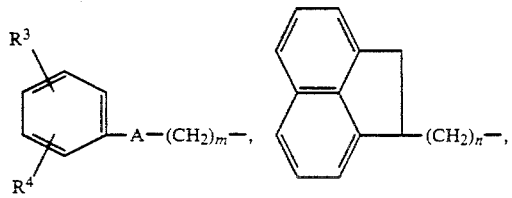

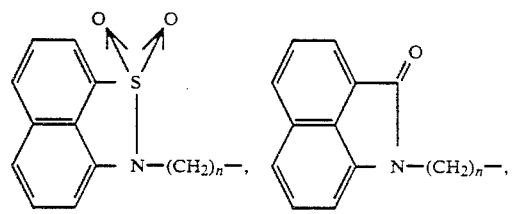

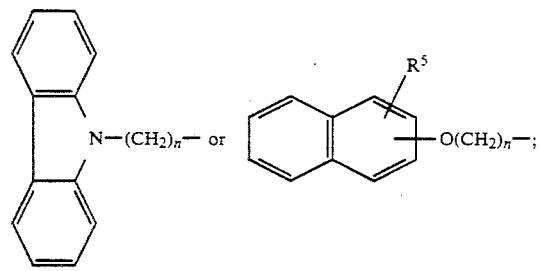

$R^1$ and $R^2$ are each, independently, hydrogen or lower alkyl;
$R^3$ and $R^4$ are each, independently, hydrogen, alkyl of 1-20 carbon atoms, halo, halo lower alkyl, halo lower alkoxy, lower alkoxy, halo lower alkylsulfonyl, nitro or trifluoromethyl, where at least one of $R^3$ and $R^4$ is other than hydrogen;
$R^5$ is hydrogen, lower alkyl or halo;
A is —$CH_2$—, —O— or —S—;
m is 0-10;
n is 1-8;
X is hydrogen, fluoro, lower alkyl or aralkyl of 7-12 carbon atoms;
or a pharmacologically acceptable salt thereof.

14 Claims, No Drawings

PHOSPHOLIPASE A2 INHIBITORS

The present invention is directed to certain alkynyl fluoroketones which are inhibitors of phospholipase $A_2$ and have anti-inflammatory activity.

It is now well-established that arachidonic acid (AA) is metabolized in mammals by two distinct pathways. The metabolism of arachidonic acid by cyclooxygenase enzymes results in the production of prostaglandins and thromboxanes. The physiological activity of the prostaglandins has already been amply elucidated in recent years. It is now known that prostaglandins arise from the endoperoxides $PGG_2$ and $PGH_2$ by the cyclooxygenase pathway of arachidonic acid metabolism. These endoperoxides are also the precursors of the thromboxanes (Tx) $A_2$ and $B_2$. $TxA_2$ is a vasoconstrictor which stimulates platelet aggregation. In the normal situation, the vasoconstrictive and platelet aggregating properties of the thromboxanes are balanced by another product arising from the endoperoxides in the cyclooxygenase pathway, prostacyclin ($PGI_2$), which is a vasodilator with platelet aggregation inhibitory activity. In the event prostacyclin synthesis is impaired and/or platelet activation is enhanced, then thrombosis and vasoconstriction is favored. The role of prostanoids in haemostasis and thrombosis are reviewed by R. J. Gryglewski, CRC Crit. Rev. Biochem., 7, 291 (1980) and J. B. Smith, Am. J. Pathol., 99, 743 (1980). Cyclooxygenase metabolites are known to participate directly in the inflammatory response [see Higgs et al., Annals of Clinical Research, 16, 287-299 (1984)]. This is through their vasodepressor activities, participation in pain and fever, augmentation of peptide mediator vascular permeability and edema forming properties. Finally, various aspects of cell mediated immunity are influenced by cyclooxygenase products.

The other pathway of AA metabolism involves lipoxygenase enzymes and results in the production of a number of oxidative products called leukotrienes. The latter are designated by the LT nomenclature system, and the most significant products of the lipoxygenase metabolic pathway are the leukotrienes $B_4$, $C_4$ and $D_4$. The substance denominated slow-reacting substance of anaphylaxis (SRS-A) has been shown to consist of a mixture of leukotrienes, with $LTC_4$ and $LTD_4$ as the primary products and having varying amounts of other leukotriene metabolites [see Bach et al., J. Immun., 215, 115-118 (1980); Biochem. Biophys. Res. Commun., 93, 1121-1126 (1980)].

The significance of these leukotrienes is that a great deal of evidence has been accumulated showing that leukotrienes participate in inflammatory reactions, exhibit chemotactic activities, stimulate lysosomal enzyme release and act as important factors in the immediate hypersensitivity reaction. It has been shown that $LTC_4$ and $LTD_4$ are potent bronchoconstrictors of the human bronchi [see Dahlen et al., Nature, 288, 484-486 (1980) and Piper, Int. Arch. Appl. Immunol., 76, suppl. 1, 43 (1985)] which stimulate the release of mucus from airways in vitro [Marom et al., Am. Rev. Resp. Dis., 126, 449 (1982)], are potent vasodilators in skin [see Bisgaard et al., Prostaglandins, 23, 797 (1982)], and produce a wheal and flare response [Camp et al., Br. J. Pharmacol., 80, 497 (1983)]. The nonpeptide leukotriene, $LTB_4$, is a powerful chemotactic factor for leukocytes [see A. W. Ford-Hutchinson, J. Roy. Soc. Med., 74, 831-833 (1981), which stimulates cell accumulation and affects vascular smooth muscle [see Bray, Br. Med. Bull., 39, 249 (1983)]. The activity of leukotrienes as mediators of inflammation and hypersensitivity is extensively reviewed in Bailey and Casey, Ann. Reports Med. Chem., 19, 87 (1986).

Phospholipase $A_2$ ($PLA_2$) is the critical rate limiting enzyme in the arachidonic acid (AA) cascade since it is responsible for the hydrolysis of esterified AA from the C-2 position of membrane phospholipids. This reaction generates two products: (1) free AA which is then available for subsequent metabolism by either the cyclooxygenase or lipoxygenase enzymes, and (2) lysophospholipid. When alkylarachidonoyl-glycerophosphatidylcholine is acted upon by the $PLA_2$ the generation of platelet activating factor (PAF) is initiated; PAF is pro-inflammatory in its own right [see Wedmore et al., Br. J. Pharmacol., 74, 916-917 (1981)]. In this regard it may be noted that the anti-inflammatory steroids are thought to inhibit eicosanoid synthesis by inducing the synthesis of a $PLA_2$ inhibitory protein denominated macrocortin, lipomodulin or lipocortin [see Flower et al., Nature, London, 278, 456 (1979) and Hirata et al., Proc. Natn. Acad. Sci. U.S.A., 77, 2533 (1980)].

As the initial step leading to subsequent conversion of AA to the various eicosanoids by the cyclooxygenase and lipoxygenase pathways, the $PLA_2$-mediated release of AA from membrane phospholipids is a critical event in attempting to deal with the various physiological manifestations which are based on the activity of the eicosanoids and/or PAF. Thus, while $PLA_2$ has been shown to be required for platelet aggregation [Pickett et al., Biochem. J., 160, 405 (1976)], cardiac contraction and excitation [Geisler et al., Pharm. Res. Commun., 9, 117 (1977)], as well as prostaglandin synthesis [Vogt, Adv. Prostagl. Thromb. Res., 3, 89 (1978)], the inhibition of $PLA_2$ is indicated in the therapeutic treatment of both PAF induced or cyclooxygenase and/or lipoxygenase pathway product-mediated physiological conditions. Thus, $PLA_2$ inhibitors are a rational approach to the prevention, removal or amelioration of such conditions as allergy, anaphylaxis, asthma and inflammation.

The invention provides novel compounds of the formula $$Z-\underset{R^1}{\underset{|}{\overset{R^2}{\overset{|}{C}}}}-C\equiv C-\overset{O}{\overset{\|}{C}}-CF_2X$$

wherein

Z is a group having the formula

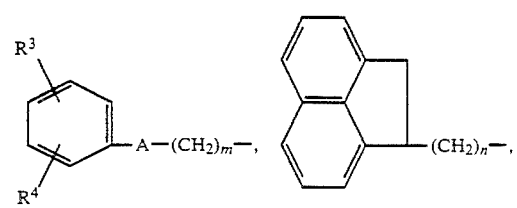

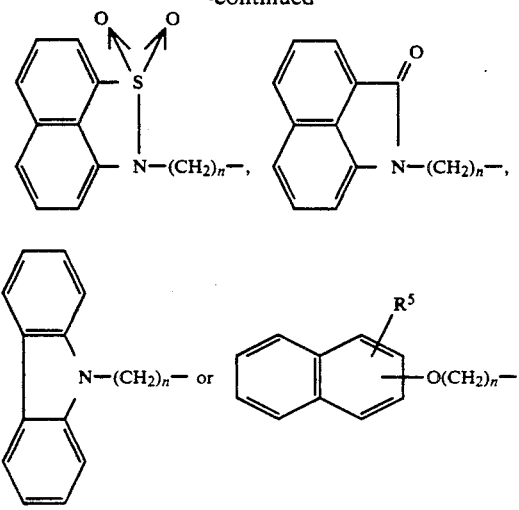

R[1] and R[2] are each, independently, hydrogen or lower alkyl;

R[3] and R[4] are each, independently, hydrogen, alkyl of 1–20 carbon atoms, halo, halo lower alkyl, halo lower alkoxy, lower alkoxy, halo lower alkylsulfonyl, nitro or trifluoromethyl, where at least one of R[3] and R[4] is other than hydrogen;

R[5] is hydrogen, lower alkyl or halo;

A is —$CH_2$—, —O— or —S—;

m is 0–10;

n is 1–8;

X is hydrogen, fluoro, lower alkyl or aralkyl of 7–12 carbon atoms;

or a pharmacologically acceptable salt thereof.

The terms "lower alkyl" and "lower alkoxy," when used alone or in combination, refer to moieties having 1 to 6 carbon atoms in the carbon chain. The term "aralkyl of 7–10 carbon atoms" refers to phenyl lower alkyl moieties. The term "halo" refers to fluoro, bromo or chloro.

The compounds within the scope of the invention can be prepared by a variety of synthetic routes using conventional methods. According to one preparative scheme, for example, a suitable phenoxide is first reacted with a haloalkyne to give a terminal alkyne intermediate.

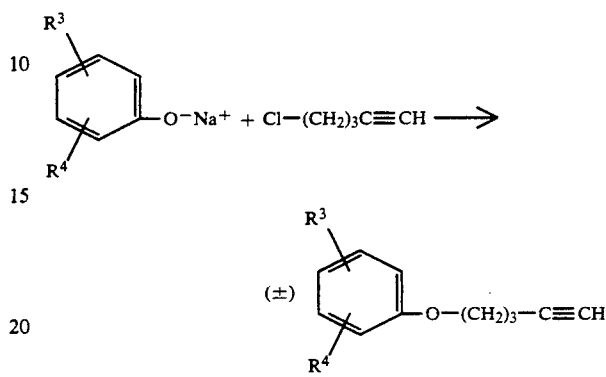

The alkyne intermediate is treated with a base, such as n-butyllithium followed by the addition of an α-fluorinated ester to yield desired final product alkynyl fluoroketones

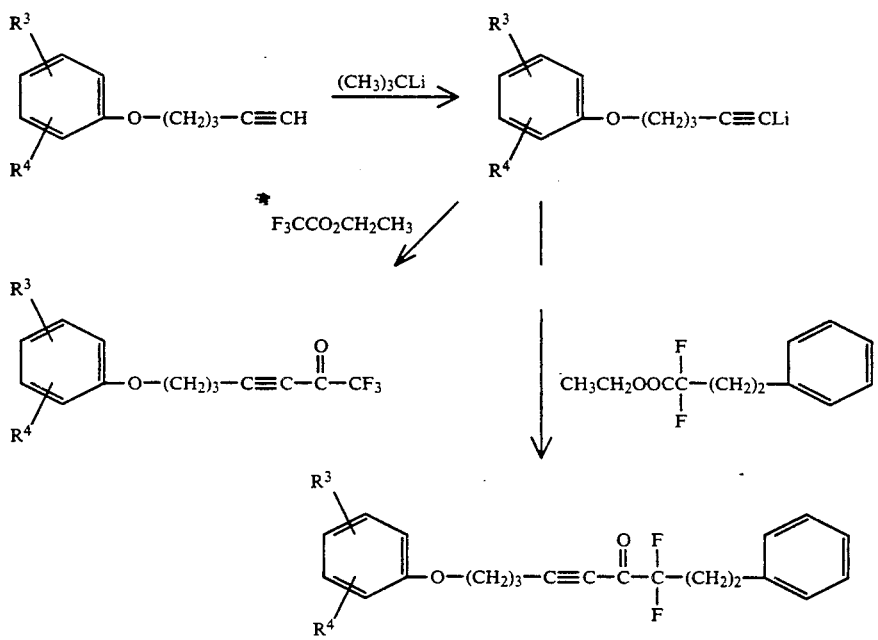

In a similar manner, reacting anions such as

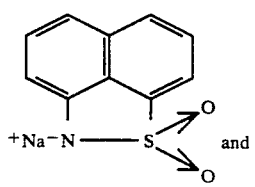

and

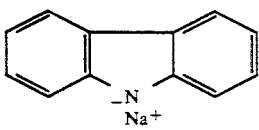

with haloalkynes as outlined above gives rise to the corresponding alkynyl fluoroketones.

The starting material α-fluorinated esters used in the above sequence can be prepared by known preparative methods. Thus, for example, α-ketoesters can be reacted with a fluorinating reagent such as diethylaminosulfur trifluoride to yield the desired α-fluorinated esters:

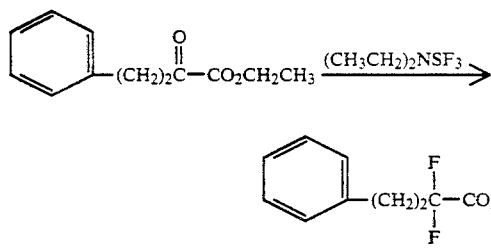

The α-ketoesters in the above reaction can be prepared from an appropriate haloalkylbenzene using a Grignard reagent and ethyl oxalyl chloride or diethyl oxalate. All other starting materials for preparing the desired final product alkynyl fluoroketones are either commercially available or can be prepared by conventional methods known in the art.

The compounds of the invention, by virtue of their ability to inhibit activity of $PLA_2$ enzyme, are useful in the treatment of conditions mediated by products of the oxidation of arachidonic acid. Accordingly, the compounds are indicated in the prevention and treatment of such conditions as allergic rhinitis, allergic bronchial asthma and other naso-bronchial obstructive air-passageway conditions, other immediate hypersensitivity reactions, such as allergic conjunctivitis; immunoinflammatory disorders, such as contact dermatitis, irritable bowel disease and the like; and various inflammatory conditions such as those present in rheumatoid arthritis, osteoarthritis, tendinitis, bursitis, psoriasis (and related skin inflammations) and the like.

When the compounds within the scope of the invention are employed in the treatment of allergic airways disorders or in anti-inflammatory therapy, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol. The compounds may also be used topically and for this purpose they may be formulated in the form of dusting powders, creams or lotions in pharmaceutically acceptable vehicles, which are applied to affected portions of the skin.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The $PLA_2$ inhibitory and anti-inflammatory activity of the compounds of the invention, may be demonstrated by standard pharmacological procedures which are described more fully in the examples given hereinafter.

These procedures, inter alia, determine the specificity of action of the compounds of the invention as $PLA_2$ inhibitors as measured by their ability to inhibit the synthesis of $LTB_4$ and $TxB_2$ by rat glycogen-elicited polymorphonuclear leukocytes, as well as measure their ability to inhibit arachidonic acid release mediated by human source $PLA_2$. The procedures further measure the ability of the compounds of the invention to inhibit, in vivo, the activity of exogenously administered $PLA_2$. The pharmacological testing additionally demonstrates the ability of the compounds of the invention to inhibit, in vivo, the lipoxygenase and cyclooxygenase pathways of arachidonic acid metabolism.

The following examples show the preparation and pharmacological testing of compounds within the invention.

EXAMPLE 1

7-(4-Chlorophenoxy)-1,1,1-trifluoro-3-heptyn-2-one

A. 1-Chloro-4-(4-pentynyloxy) benzene

To a mixture of 51.4 g (0.4 mol) of 4-chlorophenol, 49.2 g (0.48 mol) of 5-chloro-1-pentyne and 7.36 g (20 mmol) of tetra-n-butyl ammonium iodide in 140 mL of ethanol is added a solution of 24.7 g (0.44 mol) of potassium hydroxide in 24 mL of water over 2 minutes. The mixture is heated to reflux and is maintained for 25 hours.

The mixture is cooled to room temperature, diluted with water and is extracted 3 times with ethyl ether. The combined ethereal extracts are washed with 10% aqueous sodium hydroxide (3 times) and are dried over magnesium sulfate. Filtration and evaporation under reduced pressure at 50° C. gives a crude oil. Distillation at high vacuum gives 64.1 g (82%) of the title compound: bp 110°–111° C. (2.0 mm); m.p. 38°–43° C.

Analysis for: $C_{11}H_{11}ClO$: Calculated: C, 67.87; H, 5.70; Found: C, 67.62; H, 5.98.

B. 7-(4-Chlorophenoxy)-1,1,1-trifluoro-3-heptyn-2-one

To a solution of 3.88 g (20 mmol) of 1-chloro-4-(4-pentynyloxy)benzene in 40 mL of anhydrous tetrahydrofuran cooled to −78° C. under a nitrogen atmosphere is added 8.0 mL (20 mmol) of 2.5M n-butyllithium. The mixture is maintained with stirring for 1 hour and then is transferred by cannula over 30 minutes to a solution of 5.68 g (40 mmol, 4.76 mL) of ethyl trifluoroacetate in 10 mL of tetrahydrofuran cooled to −78° C. When the addition is completed, the mixture is allowed to warm to room temperature and is stirred for 2 hours.

The reaction mixture is diluted with aqueous sodium bicarbonate and is extracted with ethyl ether. The ethereal extract is washed, sequentially, with water, dilute aqueous hydrochloric acid, water and aqueous sodium bicarbonate. The extract is dried over magnesium sulfate, filtered and rotoevaporated to give crude title compound.

Flash chromatography on silica gel using hexane:ethyl ether (3:2) gives 3.77 g (64.9%) of the title compound (Rf 0.43 in hexane:ethyl ether (1:1)) as an oil: IR (film) 2203, 1709 cm$^{-1}$; NMR (CDCl$_3$) $\delta$2.12 (2H, p, J=6 Hz), 2.74 (2H, t, J=7 Hz), 4.04 (2H, t, J=6 Hz), 6.83 (2H, d, J=9 Hz) and 7.24 (2H, d, J=9 Hz).

EXAMPLE 2

7-(9H-Carbazol-9-yl)-1,1,1-trifluoro-3-heptyn-2-one

A. 9-[1-(4-Pentynyl)]9H-carbazole

To a suspension of 2.15 g (90 mmol) of sodium hydride (prepared from 4.30 g of 50% sodium hydride in mineral oil by hexane wash) in 150 mL of anhydrous dimethyl sulfoxide is added 15.0 g (90 mmol) of carbazole. The mixture is maintained with stirring at 50° C. for 2 hours at which time all hydrogen evolution has ceased. 5-Chloro-1-pentyne (10.1 g, 10.5 mL, 99 mmol) is added and the mixture is stirred overnight at room temperature.

The mixture is diluted with water and is extracted 3 times with methylene chloride. The combined organic extracts are washed with water, dried over magnesium sulfate, filtered and evaporated. The obtained residue is subjected to HPLC using silica gel as support and a hexane:ethyl acetate gradient as eluent to give 12.8 g (61%) of the title compound as a tan solid: mp 61°–64° C.; IR (film) 1600, 1450 cm$^{-1}$; NMR (CDCl$_3$) $\delta$2.09 (3H, m), 2.20 (2H, m), 4.4 (2H, t, J=7 Hz), 7.22 (4H, m, J=4 Hz), 7.45 (2H, d, J=4 Hz), 8.03 (2H, d, J=8 Hz).

B. 7-(9H-Carbazol-9-yl)-1,1,1-trifluoro-3-heptyn-2-one

To a solution of 2.0 g (9 mmol) of 9-[1-(4-pentynyl)]-9H-carbazole in 20 mL of anhydrous tetrahydrofuran cooled to −78° C. is added 3.3 mL (9 mmol) of 2.5M n-butyllithium in hexanes. The mixture is maintained at −78° C. for 1 hour and then is transferred by cannula to a solution of 3.65 g (3.06 mL, 26 mmol) of ethyl trifluoroacetate in 5 mL of anhydrous tetrahydrofuran at −78° C. After the addition is complete, the mixture is stirred for 1 hour, warmed to 0° C. and is quenched with saturated ammonium chloride. The organic layer is separated and the aqueous phase is extracted (2 times) with ethyl ether. The combined ethereal layers are washed with saturated brine, dried over magnesium sulfate, filtered and evaporated. The crude product is subjected to flash chromatography on silica gel using hexane:ethyl acetate (4:1) as eluting solvent. The appropriate fractions are combined to give the title compound as an oil: IR (film) 1730, 2220 cm$^{-1}$.

Analysis for: $C_{19}H_{14}F_3NO$: Calculated: C, 69.30; H, 4.28; N, 4.25; Found: C, 69.31; H, 4.08; N, 4.22.

EXAMPLE 3

1,1,1-Trifluoro-7-(4-fluorophenoxy)-3-heptyn-2-one

A. 1-Fluoro-4-(4-pentynyloxy) benzene

To a suspension of 960 mg (40 mmol) of sodium hydride in 50 mL of dimethyl sulfoxide is added 4.48 g (40 mmol) of 4-fluorophenol. The mixture is stirred until hydrogen evolution has ceased and then 4.10 g (40 mmol, 4.24 mL) of 5-chloro-1-pentyne is added. The mixture is heated to 65° C. for 1 hour, is diluted with water and is extracted with hexane. The hexane extract is washed with 2.5M aqueous sodium hydroxide and saturated brine and is dried over magnesium sulfate. The dried solution is filtered and rotoevaporated to give 7.1 g (99%) of title compound. IR: (film) 3310, 1508 cm$^{-1}$; $^1$H NMR (CDCl$_3$): $\delta$1.97 (1H, t, J=3 Hz), 1.99 (2H, p, J=6 Hz), 2.40 (2H, dt, J=3, 7 Hz), 4.03 (2H, t, J=6 Hz), 6.84 (2H, m) and 6.96 (2H, t, J=8 Hz).

B. 1,1,1-Trifluoro-7-(4-fluorophenoxy)-3-heptyn-2-one

Following the procedure of Example 1, the title compound is prepared.

Analysis for: $C_{13}H_{10}F_4O_2$: Calculated: C, 57.77; H, 3.70; Found: C, 56.79; H, 3.74.

EXAMPLE 4

7-[4-(1,1-Dimethylethyl)phenoxy]-1,1,1-trifluoro-3-heptyn-2-one

A. 5-[4-(1,1-Dimethylethyl)phenoxy]-1-pentyne

To a suspension of 1.01 g (42 mmol) of sodium hydride (prepared from 2.02 g of 50% sodium hydride in mineral oil by a hexane wash) in 100 mL of dimethyl sulfoxide is added portionwise at 10° C., 6.61 g (44 mmol) of 4-t-butylphenol.

When the gas evolution ceases, 4.10 g (40 mmol, 4.24 mL) of 5-chloro-1-pentyne is added and the mixture is allowed to warm to room temperature. The mixture is maintained with stirring for 22 hours, diluted with water and is extracted with ethyl ether. The ethereal extract is dried over magnesium sulfate, filtered and rotoevaporated to give the crude title compound.

An analytical sample is prepared by flash chromatography on silica gel using hexane:ethyl ether (9:1) as eluent.

Analysis for: $C_{15}H_{20}O$: Calculated: C, 83.28; H, 9.32; Found: C, 83.39; H, 9.35.

B. 7-[4-(1,1-Dimethylethyl)phenoxy]-1,1,1-trifluoro-3-heptyn-2-one

Following the procedure of Example 1, the title compound is prepared.

Analysis for: $C_{17}H_{19}F_3O_2$: Calculated: C, 65.38; H, 6.09; Found: C, 65.36; H, 6.07.

EXAMPLE 5

1,1,1-Trifluoro-7-(4-methoxyphenoxy)-3-heptyn-2-one

A. 1-Methoxy-4-(4-pentynyloxy)benzene

To a suspension of 960 mg (40 mmol) of sodium hydride in 25 mL of dimethyl sulfoxide is added 4.97 g (40 mmol) of 4-methoxyphenol. After the evolution of hydrogen has ceased, 4.10 g (40 mmol, 4.24 mL) of 5-chloro-1-pentyne is added. The mixture is maintained with stirring for 16.5 hours, is diluted with water and is extracted with ethyl ether. The ethereal extract is dried over magnesium sulfate, filtered and rotoevaporated to give 7.1 g (93%) of title compound.

Analysis for: $C_{12}H_{14}O_2$: Calculated: C, 75.79; H, 7.36; Found: C, 75.69; H, 7.58.

B. 1,1,1-Trifluoro-7-(4-methoxyphenoxy)-3-heptyn-2-one

Following the procedure of Example 1, the title compound is prepared.

Analysis for: $C_{14}H_{13}F_3O_3$: Calculated: C, 58.74; H, 4.58; Found: C, 58.55; H, 4.61.

EXAMPLE 6

1,1,1-Trifluoro-7-(2H-naphth[1,8-cd]isothiazol-2-yl)-3-heptyn-2-one S,S-dioxide

A. 2-(4-Pentynyloxy)-2H-naphth[1,8-cd]isothiazole

To a suspension of 1.75 g (73 mmol) of sodium hydride in 150 mL of dimethyl sulfoxide is added 15.0 g (73 mmol) of naphthasulfam. The mixture is stirred at 50° C. until all hydrogen evolution has ceased (1.5 h) and then 8.25 g (80 mmol, 8.5 mL) of 5-chloro-1-pentyne is added. The reaction mixture is stirred for 2 days and is then diluted with 1N aqueous hydrochloric acid and extracted with methylene chloride (3 times). The combined organic extracts are washed with water, dried over magnesium sulfate and evaporated. The obtained residue is subjected to HPLC on silica gel using a hexane:ethyl acetate gradient. Combination of the appropriate fractions gives 4.7 g (24%) of the title compound: m.p. 56°-59° C.; IR (film) 1600, 3300 cm$^{-1}$; NMR (CDCl$_3$) $\delta$2.09 (1H, t, J=3 Hz), 2.15 (2H, p, J=7 Hz), 2.43 (2H, dt, J=7, 3 Hz), 3.99 (2H, t, J=7 Hz), 6.83–8.07 (6H, arom).

B. 1,1,1-Trifluoro-7-(2H-naphth[1,8-cd]isothiazol-2-yl)-3-heptyn-2-one S,S-dioxide Following the procedure of Example 1, the title compound is prepared.

Analysis for: $C_{17}H_{12}F_3NO_3S$: Calculated: C, 55.58; H, 3.29; N, 3.81; Found: C, 55.59; H, 3.42; N, 3.73.

EXAMPLE 7

9-(4-Chlorophenoxy)-3,3-difluoro-1-phenyl-5-nonyn-4-one

A. Ethyl 2,2-difluoro-4-phenyl butanoate

A solution of 14.5 g (70 mmol) of ethyl 2-oxo-4-phenyl butanoate in 25 mL of trichlorofluoromethane cooled to 0° C. is treated with 11.5 mL of diethylaminosulfur trifluoride. The mixture is allowed to warm to room temperature and is stirred overnight. The mixture is cooled to 0° C. and is quenched cautiously with aqueous saturated sodium bicarbonate. The phases are separated and the organic phase is washed with saturated aqueous sodium bicarbonate and then with saturated brine. The ethereal extract is dried over magnesium sulfate, filtered and evaporated. The obtained residue is subjected to HPLC to give 10.2 g of the title compound (62%):

IR (film) 1770 cm$^{-1}$.

Analysis for: $C_{12}H_{14}F_2O_2$: Calculated: C, 63.15; H, 6.18; Found: C, 63.27; H, 6.27.

B. 9-(4-Chlorophenoxy)-3,3-difluoro-1-phenyl-5-nonyn-4-one

To a 3.0 g (15 mmol) of 1-chloro-4-(4-pentynyloxy) benzene of Example 1A) in 25 mL of dry tetrahydrofuran cooled to −78° C. is added 5.9 mL (15 mmol) of 2.6M n-butyllithium in hexanes. The mixture is maintained with stirring at −78° C. for 45 minutes and is transferred dropwise by cannula to a solution of 3.5 g (15 mmol) of ethyl 2,2-difluoro-4-phenyl butanoate in 10 mL of dry tetrahydrofuran cooled to −78° C. After the addition is complete, the mixture is stirred for 1.5 hours. The mixture is warmed to room temperature and is quenched with saturated aqueous ammonium chloride and ethyl ether. The layers are separated and the aqueous layer is washed (2 times) with ethyl ether. The combined ethereal extracts are washed with brine, dried over magnesium sulfate, filtered and evaporated to give a crude yellow oil.

Flash chromatography on silica gel using hexane:ethyl ether (9:1) affords 1.9 g (32%) of the title compound: IR (film) 1700, 2200 cm$^{-1}$.

Analysis for: $C_{21}H_{19}F_2ClO_2$: Calculated: C, 66.26; H, 5.03; Found: C, 66.65; H, 5.20.

EXAMPLE 8

1,1,1-Trifluoro-7-[3-(trifluoromethyl)phenoxy]-3-heptyn-2-one

To a solution of 4.56 g (20 mmol) of 1-(4-pentynyloxy)-3-trifluoromethylbenzene in 15 ml of tetrahydrofuran cooled to −78° C. under a nitrogen atmosphere is added dropwise 8 ml of n-butyllithium (2.5M in hexanes). After 1 hour, the solution is transferred by cannula to a solution of 4.76 ml (40 mmol) of ethyl trifluoroacetate in 10 ml of tetrahydrofuran cooled to −78° C. The mixture is allowed to warm to room temperature and is maintained for 1 hour.

The mixture is diluted with ethyl ether and aqueous sodium bicarbonate and is extracted with ethyl ether (3 times). The combined organic extracts are dried over magnesium sulfate, filtered and evaporated to give a crude yellow oil. Flash chromatography using hexane:ethyl ether (3:1) followed by a second chromatography using hexane:methylene chloride (3:1) as eluent affords 2.65 g of the title compound as an oil: IR (film) 2220, 1717 cm$^{-1}$; NMR (CDCl$_3$) $\delta$2.16 (2H, p, J=6 Hz), 2.77 (2H, t, J=7 Hz), 4.11 (2H, t, J=6 Hz), 7.06 (1H, dd, J=2.4, 8.4 Hz), 7.13 (1H, broad s), 7.21 (1H, d, J=7.7 Hz), 7.40 (1H, t, J=8.0 Hz).

Analysis for: $C_{14}H_{10}F_6O_2$: Calculated: C, 51.86, H, 3.11; Found: C, 52.43, H, 3.39.

EXAMPLE 9

7-(4-Chlorophenoxy)-5,5-dimethyl-1,1,1-trifluoro-3-heptyne-2-one

A. 5-(4-chlorophenoxy)-3,3-dimethyl-1-pentyne

To a solution of 5.0 g (44.6 mmol) of 3,3-dimethyl-4-pentyn-1-ol and 5.7 g (44.6 mmol) of 4-chlorophenol in 125 ml of tetrahydrofuran cooled to 0° C. is added 11.7 g (44.6 mmol) of triphenyl phosphine followed by 7.8 g (7.0 ml, 44.6 mmol) of diethyl azodicarboxylate. The reaction mixture is allowed to warm to room temperature and stirred overnight. The solvent is evaporated and the residue triturated with hexane. The solid is filtered, washed with hexane and the resulting filtrate evaporated. The residue is subjected to flash chromatography (silica gel) using hexane as eluting solvent to afford 5.0 g of colorless crystalline solid: m.p. 42°-45° C.; NMR (CDCl$_3$) $\delta$1.3 (6H, s), 1.9 (2H, t, J=6.5 Hz), 2.12 (1H, s), 4.15 (2H, t, J=6.6 Hz), 6.8 (2H, d, J=9.0 Hz), 7.2 (2H, d, J=9.0 Hz).

B. 7-(4-chlorophenoxy)-5,5-dimethyl-1,1,1-trifluoro-3-heptyne-2-one

To a solution of 2.5 g (11.2 mmol) of 5-(4-chlorophenoxy)-3,3-dimethyl-1-pentyne in 25 ml of anhydrous tetrahydrofuran cooled to −78° C. under a nitrogen atmosphere is added 4.5 ml of 2.5M n-butyllithium in hexanes. The mixture is stirred at −78° C. for 1 hour and then is transferred by canula to a solution of 3.19 g (22.4 mmol) of ethyl trifluoroacetate in 10 ml of tetrahydrofuran cooled to −78° C. After the addition is complete, the reaction is stirred at −78° C. for 0.5 hour, is allowed to warm to 0° C. and then is quenched with saturated ammonium chloride followed by 0.1N hydrochloric acid. The layers are separated and the organic phase is washed with saturated sodium bicarbonate and brine. The organic extract is dried over magnesium sulfate, filtered and evaporated. The residue is subjected to flash chromatography on silica gel using hexane:ethyl ether (93:7) as eluting solvent. The appropriate fractions are combined and evaporated to give a light tan oil: IR (film) 2200, 1710 cm$^{-1}$; NMR (CDCl$_3$) δ1.42 (6H, s), 2.04 (2H, d, J=6.5 Hz), 4.1 (2H, t, J=6.6 Hz), 6.81 (2H, d, J=9.0 Hz), 7.23 (2H, d, J=9.0 Hz)

Analysis for: C$_{15}$H$_{16}$F$_3$ClO$_2$: Calculated: C, 56.61; H, 4.40; Found: C, 56.30; H, 4.32.

EXAMPLE 10

8-(4-Chlorophenoxy)-1,1,1-trifluoro-3-octyn-2-one

A solution of 4.16 g (20 mmol) of 1-chloro-4-(5-hexynyloxy)benzene in 50 ml of tetrahydrofuran cooled to −78° C. is treated with 8.8 ml of n-butyllithium (2.5M in hexanes) and is maintained with stirring for 1.5 hours.

The mixture is treated dropwise with 3.13 g (22 mmol) of ethyl trifluoroacetate, is allowed to warm to room temperature and is maintained with stirring for 17 hours.

The mixture is diluted with 0.1N hydrochloric acid and is extracted with ethyl ether (3 times). The combined ethereal extracts are washed with aqueous sodium bicarbonate and are dried over magnesium sulfate, filtered and evaporated to give a crude oil. Flash chromatography using hexane:methylene chloride (65:35) as eluent gives partially purified material which is resubjected to flash chromatography using hexane: ethyl ether (9:5) as eluting solvent to give the title compound as an oil: IR (film) 2195, 1705 cm$^{-1}$; NMR (CDCl$_3$) δ1.89 (4H, m), 2.60 (2H, t, J=7.0 Hz), 3.97 (2H, t, J=5.8 Hz), 6.81 (2H, d, J=9.0 Hz), 7.23 (2H, d, J=9.0 Hz).

Analysis for: C$_{14}$H$_{12}$ClF$_3$O$_2$: Calculated: C, 55.19, H, 3.97; Found: C, 54.10, H, 3.86.

EXAMPLE 11

7-[(4-Chloro-1-naphthalenyl)oxy]-1,1,1-trifluoro-3-heptyn-2-one

A. 1-chloro-4-(4-pentynyloxy)naphthalene

In the same manner as that described in Example 1A is prepared the title compound with the exception that 4-chloro-1-napthol is used instead of 4-chlorophenol.

Analysis for: C$_{15}$H$_{13}$ClO: Calculated: C, 73.62; H, 5.35; Found: C, 73.70; H, 5.47.

B. 7-[(4-Chloro-1-naphthalenyl)oxy]-1,1,1-trifluoro-3-heptyn-2-one

To a solution of 2.4 g (10 mmol) of 1-chloro-4-(4-pentynyloxy)naphthalene in 20 ml of tetrahydrofuran cooled to −78° C. is added dropwise 4 ml of 2.5M n-butyllithium in hexanes. The mixture is allowed to warm to 0° C. and is maintained for 1 hour.

The mixture is cooled to −78° C. and 2.84 g (20 mmol, 2.37 ml) of ethyl trifluoroacetate is introduced dropwise. The mixture is allowed to warm to room temperature and is stirred overnight (15 hours).

The mixture is diluted with aqueous sodium bicarbonate and is extracted with ethyl ether. The combined ethereal extracts are dried over magnesium sulfate, filtered and evaporated to give crude product. The product is subjected to flash chromatography on silica gel using hexane:ethyl ether (3:2) as eluent. The obtained product was triturated with hexane, filtered and dried over phosphorus pentoxide under high vacuum. Recrystallization from hexane (3 times) gives 280 mg of the title compound: mp 44°–46° C.; IR (KBr) 2215, 1712 cm$^{-1}$; NMR (CDCl$_3$) δ2.27 (2H, p, J=6 Hz), 2.83 (2H, T, J=7 Hz), 4.22 (2, t, J=5.7 Hz), 6.71 (1H, d, J=8.3 Hz), 7.43 (1H, d, J=8.1 Hz), 7.52 (1h, t, J=7.6 Hz), 7.61 (1H, t, J=7.6 Hz). 8.19 (1H, d, J=8.3 Hz), 8.23 (1H, d, J=8.3 Hz).

Analysis for: C$_{17}$H$_{12}$F$_3$ClO$_2$: Calculated: C, 59.93; H, 3.55; Found: C, 59.90, H, 3.46.

EXAMPLE 12

1,1,1-Trifluoro-5-methyl-5-[4-(trifluoromethoxy)phenoxy]-3-hexyn-2-one

To a solution of 1.47 g (6 mmol) of 1-(1,1-dimethyl-2-propynyloxy)-4-trifluoromethoxybenzene in 25 ml of tetrahydrofuran cooled to −78° C. is added 2.4 ml of n-butyllithium (2.5M in hexanes). The solution is maintained with stirring for 1 hour. The mixture is treated with 1.70 g (12 mmol, 1.43 ml) of ethyl trifluoroacetate at −78° C. and is allowed to warm to room temperature. After stirring for 1 hour, the mixture is diluted with water and is extracted with ethyl ether (3 times). The combined ethereal extracts are washed with aqueous sodium bicarbonate, dried over magnesium sulfate, filtered and evaporated to give a light oil. Flash chromatography using hexane:ethyl ether (65:35) affords the title compound: IR (film) 2215, 1740 cm$^{-1}$; NMR (CDCl$_3$) δ1.73 (6H, s), 7.16 (4H, m).

EXAMPLE 13

1,1,1-Trifluoro-5-(3-pentadecylphenoxy)-3-pentyn-2-one

A. 3-Pentadecyl-1-(2-propynyloxy)benzene

To a solution of 24.4 g (80 mmol) of 3-pentadecylphenol, 4.93 g (88 mmol) of propargyl alcohol and 23.1 g (88 mmol) of triphenylphosphine cooled to 15° C. is added dropwise 15.3 g (13.9 ml, 88 mmol) of diethyl azodicarboxylate. The mixture is stirred for 4.5 hours and then is diluted with water and extracted with hexane (3 times). The hexane extracts are combined, washed with 1N sodium hydroxide and are dried over magnesium sulfate overnight. Filtration and evaporation gives crude oil which is subjected to flash chromatography using hexane as eluting solvent. The appropriate fractions are combined to give the title compound as an oil which solidifies upon standing: mp. 26°–27° C. The product is used without further characterization.

B. 1,1,1-Trifluoro-5-(3-pentadecylphenoxy)-3-pentyn-2-one

To a solution of 6.85 g (20 mmol) of 3-pentadecyl-1-(2-propynyloxy)benzene in 150 ml of tetrahydrofuran cooled to −78° C. is added 8.0 ml (20 mmol) of 2.5M n-butyllithium. After 30 minutes, 5.68 g (4.76 ml, 40 mmol) of ethyl trifluoroacetate is added and the mixture is allowed to come to room temperature. After 1 hour, the mixture is diluted with water and is extracted with ethyl ether (3 times). The combined ethereal extracts are dried over magnesium sulfate, filtered and evaporated to give crude product.

Flash chromatography on silica gel using hexane:ether (3:2) as eluent affords the title compound as an oil which solidifies to a waxy solid following overnight drying under high vacuum: mp. 35°-36° C.; IR (KBr) 2210, 1723 cm$^{-1}$; NMR (CDCl$_3$) δ0.87 (3H, t, J=6.9 Hz), 1.25 (H, s), 1.29 (2H, bs), 1.59 (2H, m), 2.58 (2H, t, J=7.8 Hz), 4.93 (2H, s), 6.76 (1H, m), 6.78 (1H, bs), 6.87 (1H, d, J=7.8 Hz), 7.22 (1H, t, J=8.0 Hz).

Analysis for: $C_{26}H_{37}F_3O_2$: Calculated: C, 71.20; H, 8.50; Found: C, 71.36, H, 8.40.

EXAMPLE 14

The compounds 5- and 12-hydroxyeicosatetraenoic acid (5-HETE and 12-HETE) and LTB$_4$ are early arachidonic acid oxidation products in the lipoxygenase cascade, which have been shown to mediate several aspects of inflammatory and allergic response. This is especially true with respect to 5,12-diHETE, which is also denoted as LTB$_4$ [see Ford-Hitchinson, *J. Roy. Soc. Med.*, 74, 831 (1981)]. Compounds which inhibit the PLA$_2$-mediated release of arachidonic acid thereby effectively prevent the oxidation of arachidonic acid to the various leukotriene products via the lipoxygenase cascade. Accordingly, the specificity of action of PLA$_2$ inhibitors can be determined by the activity of test compounds in this assay, which measures the ability of compounds to inhibit the synthesis of LTB$_4$ by rat glycogen-elicited polymorphonuclear leukocytes (PMN) in the presence of exogenous substrate.

The assay is carried out as follows:

Rat polymorphonuclear leukocytes (PMNs) are obtained from female Wistar rats (150–200 g) which receive an injection of 6% glycogen (10 ml i.p.). Rats are sacrificed 18-24 hours post injection by CO$_2$ asphyxiation and the elicited cells are harvested by peritoneal lavage using physiological saline (0.9% NaCl). The exudate is centrifuged at 400 xg for 10 minutes. The supernatant fluid is discarded and the cell pellet is resuspended to a concentration of 2.0×10$^7$ cells/mL in HBSS containing Ca$^{++}$ and Mg$^{++}$ and 10 μM L-cysteine.

To 1 mL aliquots of cell suspension, test drugs or vehicle are added, then preincubated at 37° C. for 10 minutes. A23187 (1 μM), [$^3$H]-AA (3.0 μCi/mL) and unlabeled AA (1 μM) are then added and the samples are further incubated for 10 minutes. The reaction is terminated by centrifugation and pelleting cells. Supernatants are then analyzed by HPLC analysis on a 15 cm×4.6 mm ID supelcosil LC-18 (Supelco)(3M) column, using a two solvent system at a flow rate of 1.4 mL total flow as follows:

Solvent A: 70:30 17.4 mM H$_3$PO$_4$:CH$_3$CN
Solvent B. CH$_3$CN
Gradient: (system is equilibrated with Solvent A)

| Time | Percent A | Percent B |
|---|---|---|
| 0 | 100 | 0 |
| 15.0 | 100 | 0 |
| 20.0 | 65 | 35 |
| 40.0 | 65 | 35 |
| 42.0 | 10 | 90 |
| 50.0 | 10 | 90 |
| 50.1 | 100 | 0 |

Percent solvent changes are accomplished in a linear fashion.
Injections:

140 μL of each supernatant is injected directly onto column and $^3$H arachidonic acid metabolites are monitored using an on-line radioactivity detector (Ramona, IN/US, Fairfield, N.J.).

Standards:

10$^4$–2.0×10$^4$ dpm of eicosanoids of interest are injected in 90 μL EtOH cocktail.

Co-chromatography with standard [$^3$H] leukotriene B$_4$ (LTB$_4$) in medium of stimulated PMN exposed to drug is compared to that found in medium of stimulated cells exposed to no drug, generating percent inhibition.

Results are expressed as percent inhibition at a given compound dose or as an IC$_{50}$ value.

Testing compounds of the invention in this assay gave the following results:

TABLE I

| Compound of Example No. | % Inhibition |
|---|---|
| 1 | 89.8 (at 10 μM) |
| 7 | 72 (at 10 μM) |

EXAMPLE 15

The procedure of Example 14 is also employed for the determination of the extent to which compounds of the invention inhibit the synthesis of the arachidonic acid cyclooxygenase oxidation product T×B$_2$.

In this assay, the procedure of Example 14 is carried out as described. However, in order to determine cyclooxygenase activity, the samples are co-chromatographed with authentic reference [$^3$H]-T×B$_2$.

The results are calculated as in Example 14 and presented below:

TABLE II

| Compound of Example No. | % Inhibition |
|---|---|
| 1 | 24 (at 10 μM) |
| 7 | 40 (at 10 μM) |

EXAMPLE 16

The compounds of the invention are tested in an in vitro isolated phospholipase A$_2$ assay to determine the ability of the test compounds to inhibit the release of arachidonic acid from an arachidonic acid-containing substrate by the action of phospholipase A$_2$ enzyme from human and non-human sources.

This assay is carried out as follows:

Into a 15 mL polypropylene tube are added the following:

| Agent | Volume, μL | Final Conc. |
|---|---|---|
| $^3$H-AA E. coli substrate[1] | 25 | 5 nmoles PL |
| CaCl$_2$ (0.1M)[2] | 5 | 5 mM |
| Tris-HCl (0.5M) pH 7.5[3] | 20 | 100 mM |
| Water[4] | 25 | |
| Drug/vehicle[5] | 1 | 50 μM |
| PLA$_2$ | 25 | Volume yielding 12% |

-continued

| Agent | Volume, μL | Final Conc. |
|---|---|---|
|  | 100 | hydrolysis in 10 min. |

*pre-incubate at room temperature 30 min prior to substrate addition.
[1]Prepared by adding 2 mL deionized and distilled water to 2 mL $^3$H-arachidonate labeled *E. coli* (lower count), to which is added 1 mL of $^3$H-arachidonate labeled *E. coli* (higher count) to yield a total of 5 m substrate (containing 1000 nmoles phospholipid).
[2]Stock 0.1 m $CaCl_2$, required for enzyme activity.
[3]Stock 0.5 m Trisma-Base.
Stock 0.5 M Trisma-HCl. Adjust pH to 7.5 (optimum for enzyme).
[4]Deionized and distilled water.
[5]Stock 10 mM prepared in dimethyl sulfoxide. Make 1:2 dilution with dimethyl sulfoxide and add 1 μL to 100 μL assay tube.
[6]Two human $PLA_2$ enzymes are used:
a) Semi-purified human platelet acid extract $PLA_2$ (in 10 mM sodium acetate buffer, pH 4.5). Remove protein precipitate by centrifugation at about 2200 rpm for 10 minutes.
b) Purified human synovial fluid.

Incubate the 100 μL reaction mixture for 10 minutes at 37° C. in a shaking water bath. The reaction is terminated by the addition of 2 mL tetrahydrofuran, followed by vortexing. $NH_2$ columns (100 μg/mL-Analytichem International) are conditioned with 0.5 mL tetrahydrofuran followed by 0.5 mL tetrahydrofuran/water (2 mL:0.1 mL, v/v).

The sample is loaded onto the columns and slowly drawn through them. The hydrolyzed arachidonic acid retained in the columns is eluted therefrom with 1 mL tetrahydrofuran/glacial acetic acid (2%). The arachidonic acid is transferred to scintillation vials and quantitated by β-counting analysis. A "total counts" sample is prepared by pipetting 25 μL $^3$H-arachidonate *E. coli* directly into a scintillation vial to which is added 1 mL tetrahydrofuran. 10 mL aquasol (scintillation cocktail) is added to all samples.

Calculations:

$$\% \text{ hydrolysis} = \frac{[3H]AA \text{ dpm(sample)} - [3H]AA \text{ dpm(nonspecific hydrolysis)}}{\text{total counts dpm}}$$

$$\% \text{ change} = \frac{\text{vehicle dpm} - \text{drug dpm}}{\text{vehicle dpm}} \times 100$$

Activity of Standard Drugs:

| | $IC_{50}$ (μM) | |
|---|---|---|
| Drug | Human Platelet $PLA_2$ | Human Synovial $PLA_2$ |
| Arachidonic Acid | 8.6 | 3.2 |
| Monoalide | 25.2 | 0.14 |

When tested in this assay, the compounds of the invention gave the following results:

TABLE III

| Compound of Example No. | % Inhibition at 10 μM HP* | HSF** | $IC_{50}$ (μM) HP | HSF |
|---|---|---|---|---|
| 1 | 54 (at 50 μM) |  | — | 0.49 |
| 2 | 7.2 |  |  | 0.043 |
| 3 |  |  |  | 8.9 |
| 4 |  |  |  | 0.20 |
| 5 |  | 38.7 |  |  |
| 6 |  | 84.8 |  |  |
| 7 |  |  |  | 0.90 |
| 8 |  | 90.5 |  |  |
| 9 |  | 19.8 |  |  |
| 10 |  | 94.2 |  |  |
| 11 | 26.5 | 94.6 |  |  |
| 12 |  | 58.8 |  |  |

*human platelet
**human synovial fluid

EXAMPLE 17

The ability of the compounds of the invention to inhibit paw edema induced by the exogenous administration of $PLA_2$ is measured in the in vivo $PLA_2$ murine paw edema assay.

The assay is carried out as follows:

Non-fasted, male CD-1 mice (8 weeks old; 31–36 grams) are placed in plastic boxes in groups of six. The right hind paw volume is measured using mercury plethysmography (zero time). Compounds are dosed orally (0.5 mL of 0.5% Tween-80) 1 or 3 hours prior to $PLA_2$ injection or intravenously (0.2 mL in 0.3% dimethylsulfoxide/saline) 3 minutes prior to $PLA_2$ injection. A solution of purified $PLA_2$, from the diamond back cotton mouth snake (*A. piscivorus piscivorus*) is prepared in saline at a concentration of 6 μg/mL. Fifty (50) μL (0.3 μg) of this $PLA_2$ solution is injected subcutaneously into the right hind paw with a plastic 1 mL plastic syringe (27 gauge, 1" needle). Paw volume of the injected paw is measured again at 10 minutes, 30 minutes and 60 minutes after $PLA_2$ injection. Animals are euthanized with $CO_2$ at the completion of the study.

The paw edema is calculated by subtracting the zero time volume from the volume recorded at each time period. Mean paw edema for each treatment group is then calculated and expressed as (μL±S.E.). Drug effects are expressed as a percent change from control (vehicle) values. Statistical significance is determined by a oneway analysis of variance with LSD comparison to control (p<0.05). $ED_{50}$'s are determined using repression analysis.

The activity of standard drugs in this assay is as follows:

| Compound | $ED_{50}$ mg/kg p.o. at +10 min. |
|---|---|
| Cyproheptadine | 3.1 |
| BW755C | 50 |
| Dexamethasone* | 10 |
| Naproxen | 18 |
| Aristolochic Acid** | Not Active |
| Luffarrellolide** | Not Active |

*p.o. - 3 hr.
**Some activity (30% inhibition) only when co-injected with enzyme.

When tested in this assay, the compounds of the invention gave the following results:

TABLE IV

| Compound of Example No. | Dose mg/kg | % Change in Edema | | | $ED_{50}$ mg/kg |
|---|---|---|---|---|---|
|  |  | 10 min | 30 min | 60 min |  |
| 1 | 10 (i.v.)* | −64 | −34 | −39 | 3 (i.p.)*** |
|  | 100 (p.o.)** | −26 | −37 | −23 |  |
| 2 |  |  |  |  | 1 (i.p.) |
| 3 |  |  |  |  | 30 (i.p.) |
| 4 | 30 (i.p.) | −45 |  |  |  |
| 7 |  |  |  |  | 3 (i.p.) |

*intravenous
**peroral
***intraperitoneal

The results show that the compounds of the invention are effective in vivo in inhibiting edema induced by the exogenous administration of snake venom $PLA_2$.

EXAMPLE 18

The compounds of the invention are evaluated for their ability to inhibit the lipoxygenase and/or cyclooxygenase pathways of arachidonic acid metabolism in the in vivo murine zymosan peritonitis assay.

This assay is carried out as follows:

Male CD-1 mice (8 weeks old) are placed in plastic boxes in groups of six. Animals are injected with 1 mL i.p. of either 1% zymosan in pyrogen free 0.9% saline or saline (unstimulated control). Compounds are dosed orally 1 hour prior to zymosan injection. Twenty minutes after zymosan injection, the mice are asphyxiated by $CO_2$ inhalation and the peritoneal cavity is lavaged with 2 mL ice cold Hanks Balanced Salt Solution (HBSS) without $CaCl_2$, $MgSO_4 \cdot 7H_2O$ and $MgCl_2 \cdot 6H_2O$. Peritoneal lavage fluid from each mouse is removed by syringe and placed in 5 mL plastic test tubes put on ice and volume is noted. Preparation of samples for evaluation by ELISA is as follows: Samples are centrifuged at 800 xg for 15 minutes; 1 mL of the supernatant is added to 8 mL ice cold methanol and kept at $-70°$ C. overnight to precipitate protein; and samples are then centrifuged at 800 xg for 15 minutes, followed by a drying procedure in a Savant speed vac concentrator. The samples are reconstituted with 1 mL ice cold ELISA buffer and stored at $-70°$ C. until assayed. The assay for eicosanoids ($LTC_4$ and 6-keto-$PGF_{1\alpha}$) is performed according to conventional ELISA procedures.

Compounds to be tested orally are suspended in 0.5% Tween 80. Compounds to be tested intraperitoneally are suspended in 0.5% methylcellulose in 0.9% saline.

The total metabolite level in lavage fluid/mouse is calculated and the significance is determined by a one-way analysis of variance with LSD comparisons to control ($p \leq 0.05$). Drug effects are expressed as a percent change from control values.

The activity of standard drugs in this assay is as follows:

| Compound | $ED_{50}$ mg/kg p.o. | |
| --- | --- | --- |
| | $LTC_4$ | 6-keto-$PGF_{1\alpha}$/$TxB_2$ |
| BW755C | <10 | 22.0 |
| Phenidone | 24.0 | <30.0 |
| Indomethacin | Not Active | 0.126 |
| Ibuprofen | Not Active | 7.0 |

When tested in this assay a compound of the invention and the antiinflammatory compound etodolac gave the following results:

TABLE V

| Compound of Example No. | Dose mg/kg | % Inhibition | |
| --- | --- | --- | --- |
| | | $LTC_4$ | 6-keto-PGF |
| 1 | 100 (p.o.) | 32 | 15 |

*perorally administered
**negative values denote potentiation

The results show that the compounds of the invention exert an inhibitory effect on both the lipoxygenase pathway and the cyclooxygenase pathway.

What is claimed is:

1. A compound having the formula

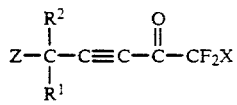

wherein

Z is a group having the formula

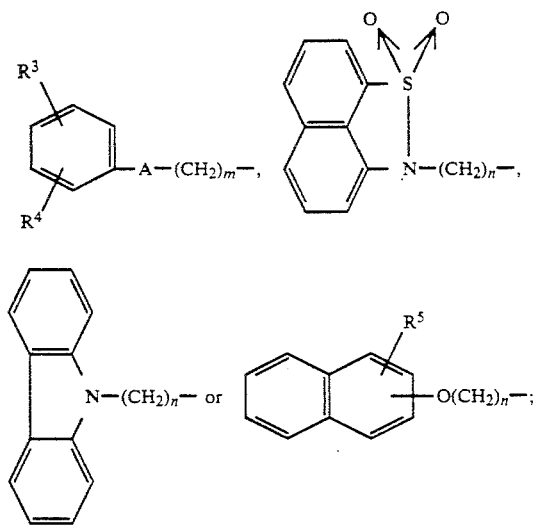

$R^1$ and $R^2$ are each, independently, hydrogen or lower alkyl;

$R^3$ and $R^4$ are each, independently, hydrogen, alkyl of 1-20 carbon atoms, halo, halo lower alkyl, halo lower alkoxy, lower alkoxy, halo lower alkylsulfonyl, nitro or trifluoromethyl, where at least one of $R^3$ and $R^4$ is other than hydrogen;

$R^5$ is hydrogen, lower alkyl or halo;

A is $-CH_2-$, $-O-$ or $-S-$;

m is 0-10;

n is 1-8;

X is hydrogen, fluoro, lower alkyl or aralkyl of 7-12 carbon atoms;

or a pharmacologically acceptable salt thereof.

2. A compound of claim 1 having the name 7-(4-chlorophenoxy)-1,1,1-trifluoro-3-heptyn-2-one.

3. A compound of claim 1 having the name 7-(9H-carbazol-9-yl)-1,1,1-trifluoro-3-heptyn-2-one.

4. A compound of claim 1 having the name 1,1,1-trifluoro-7-(4-fluorophenoxy)-3-heptyn-2-one.

5. A compound of claim 1 having the name 7-[4-(1,1-dimethylethyl)phenoxy]-1,1,1-trifluoro-3-heptyn-2-one.

6. A compound of claim 1 having the name 1,1,1-trifluoro-7-(4-methoxyphenoxy)-3-heptyn-2-one.

7. A compound of claim 1 having the name 1,1,1-trifluoro-7-(2H-naphth[1,8-cd]isothiazol-2-yl)-3-heptyn-2-one S,S-dioxide.

8. A compound of claim 1 having the name 9-(4-chlorophenoxy)-3,3-difluoro-1-phenyl-5-nonyn-4-one.

9. A compound of claim 1 having the name 1,1,1-trifluoro-7-[3-(trifluoromethyl)phenoxy]-3-heptyn-2-one.

10. A compound of claim 1 having the name 7-(4-chlorophenoxy)-5,5-dimethyl-1,1,1-trifluoro-3-heptyne-2-one.

11. A compound of claim 1 having the name 8-(4-chlorophenoxy)-1,1,1-trifluoro-3-octyn-2-one.

12. A compound of claim 1 having the name 7-[(4-chloro-1-naphthalenyl)oxy]-1,1,1-trifluoro-3-heptyn-2-one.

13. A compound of claim 1 having the name 1,1,1-trifluoro-5-methyl-5-[4-(trifluoromethoxy)phenoxy]-3-hexyn-2-one.

14. A compound of claim 1 having the name 1,1,1-trifluoro-5-(3-pentadecylphenoxy)-3-pentyn-2-one.

* * * * *